US008574889B1

(12) United States Patent
Latvala et al.

(10) Patent No.: US 8,574,889 B1
(45) Date of Patent: Nov. 5, 2013

(54) METHOD FOR PROCESSING BIOLOGICAL MATERIAL

(71) Applicant: Ductor Oy, Helsinki (FI)

(72) Inventors: Veikko Latvala, Vahto (FI); Ari Ketola, Espoo (FI); Ilona Oskanen, Helsinki (FI); Kerttu Koskenniemi, Helsinki (FI); Maiju Laaksonen, Helsinki (FI); Elisa Lensu, Espoo (FI)

(73) Assignee: Ductor Oy, Helsinki (FI)

( * ) Notice: Subject to any disclaimer, the term of this patent is extended or adjusted under 35 U.S.C. 154(b) by 0 days.

(21) Appl. No.: 13/722,228

(22) Filed: Dec. 20, 2012

Related U.S. Application Data

(60) Provisional application No. 61/659,467, filed on Jun. 14, 2012.

(51) Int. Cl.
*C12S 3/00* (2006.01)
*C12P 3/00* (2006.01)
*C12N 1/20* (2006.01)

(52) U.S. Cl.
USPC ........ 435/267; 435/168; 435/128; 435/252.1; 435/822

(58) Field of Classification Search
None
See application file for complete search history.

(56) References Cited

U.S. PATENT DOCUMENTS

| 6,716,351 | B2 | 4/2004 | Fassbender |
| 2011/0126455 | A1 | 6/2011 | Shinohara |
| 2011/0126457 | A1 | 6/2011 | Shinohara |

FOREIGN PATENT DOCUMENTS

| CN | 1308036 A | 8/2001 |
| CN | 102112609 A | 6/2011 |
| JP | 6-191976 A | 7/1994 |
| JP | 2009279534 A | 12/2009 |
| JP | 2011240254 A | 12/2011 |

OTHER PUBLICATIONS

Barros Soares et al. "Influence of some commercial proteases and enzymatic associations on the hydrolytic solubilization of deboned poultry meat proteins". Food Science and Technology International, (Aug. 2000), vol. 6, No. 4, pp. 301-306.*
Bladen, H. A., M. P. Bryant, and R. N. Doetsch. 1961. A study of bacterial species from the rumen which produce ammonia from protein hydrolysate. *Appl. Microbiol.* 9: 175-180 (6 pages).
Hungate R.E. 1969. A Roll Tube Method for Cultivation of Strict Anaerobes in *Methods of Microbiology*, vol. 111pp. 117-132, Academic Press, London (9 pages).
Vince AJ, Burridge SM. 1980. Ammonia production by intestinal bacteria: the effects of lactose, lactulose and glucose. *J Med Microbiol* 13: 177-91 (15 pages).

Russell, J. B., H. J. Strobel, and G. Chen. 1988. Enrichment and isolation of a ruminal bacterium with a very high specific activity of ammonia production. *Appl. Environ. Microbiol.* 54:872-877 (6 pages).
Chen, G., and J. B. Russell. 1988. Fermentation of peptides and amino acids by a monensin-sensitive ruminal *Peptostreptococcus*. *Appl. Environ. Microbiol.* 54:2742-2749 (8 pages).
Paster, B. J., J. B. Russell, C. M. J. Yang, J. M. Chow, C. R. Woese, and R. Tanner. 1993. Phylogeny of the ammonia-producing ruminal bacteria *Peptostreptococcus anaerobius*, *Clostridium sticldandii* and *Clostridium aminophilum* sp. nov. *Int. J. Syst. Bacteriol.* 43: 107-110 (4 pages).
Attwood et al. 1998 "Ammonia-Hyperproducing Bacteria from New Zealand Ruminants", Applied and Environmental Microbiology, May 1998, p. 1796-1804 (10 pages).
Rychlik, J. L., and J. B. Russell. 2000. Mathematical estimations of hyper-ammonia producing ruminal bacteria and evidence for bacterial antagonism that decreases ruminal ammonia production. *FEMS Microbiol. Ecol.* 32: 121-128 (8 pages).
Schulze-Rettmer, R., von Fircks, R. & Simbach, B. 2001. MAP precipitation—pilot plant investigation in Germany. *Environmental Technology* (10 pages).
Smil, V. 2001. Evolution of Ammonia Synthesis. In: Enriching the Earth. Fritz Haber, Carl Bosch, and the Transformation of World Food Production. p. 109-132. MIT Press. Cambridge (USA), London. ISBN 0-262-19449-X (15 pages).
Navarrete del Toro MA, Garda-Carrěno FL. 2002. Evaluation of the Progress of Protein Hydrolysis. *Current Protocols in Food Analytical Chemistry* B2.2.1-B2.2.14 (14 pages).
Eschenlauer, S. C. P., N. McKain, N. D. Walker, N. R. McEwan, C. J. Newbold, and R. J. Wallace. 2002. Ammonia production by rumen microorganisms and enumeration, isolation, and characterization of bacteria capable of growth on peptides and amino acids from the sheep rumen. *Appl. Environ. Microbiol.* 68:4925-4931 (8 pages).
Nelson, N.O., Mikkelsen, R.L. & Hesterberg, D. L. 2003. Struvite precipitation in anaerobic swine lagoon liquid: effect of pH and Mg:P ratio and determination of rate constant. *Bioresource Technology* 89: 229-236 (8 pages).
Whitehead TR, Cotta MA. 2004. Isolation and identification of hyper-ammonia producing bacteria from swine manure storage pits. *Curr Microbiol* 48: 20-26 (7 pages).

(Continued)

*Primary Examiner* — Vera Afremova
(74) *Attorney, Agent, or Firm* — Robebert P. Michal; Lucas & Mercanti, L.L.P.

(57) ABSTRACT

The invention provides a process for producing ammonia or ammonium from an organic material, the method by contacting the organic material with at least one hydrolytic enzyme, in a medium, to produce a medium including hydrolyzed or partially hydrolyzed organic material suitable for microbial fermentation. The hydrolyzed or partially hydrolyzed medium with organic material is then fermented in the presence of at least one microorganism capable of ammonification, wherein the fermenting is under conditions, and for a sufficient period of time, to produce a fermentation product that comprises ammonia or ammonium. The organic material includes nitrogenous compounds suitable for conversion to ammonia or ammonium.

23 Claims, 6 Drawing Sheets

(56) References Cited

OTHER PUBLICATIONS

Gowariker, V., Krishnamurthy V. N., Gowariker S., Dhanorkar, M., Kalyani P. 2009. Ammonification. In: The Fertilizer Encyclopedia. p. 41-42. John Wiley & Sons, Inc., Hoboken, New Jersey (4 pages).

Guštin S., Marinšek-Logar R. 2011. Effect of pH, temperature and air flow rate on the continuous ammonia stripping of the anaerobic digestion effluent. *Process Safety and Environmental Protection* 89: 61-66 (6 pages).

Chourey, K.; Jansson, J.; VerBerkmoes, N.; Shah, M.; Chavarria, K. L.; Tom, L. M.; Brodie, E. L.; Hettich, R. L. 2010. Direct cellular lysis/protein extraction protocol for soil metaproteomics. *Journal of Proteome Research* 9: 6615-6622 (8 pages).

US Geological Survey. 2012. Nitrogen (fixed)—ammonia. US Department of Interior, Mineral Commodity Summaries, p. 112-113. US Department of Interior, US Geological Survey (8 pages).

Opinion on Patentability dated Mar. 19, 2013 issued by the National Board of Patents and Registration of Finland in related Finnish Patent Application No. 20125661 (5 pages).

Search Report dated Mar. 19, 2013 issued by the National Board of Patents and Registration of Finland in related Finnish Patent Application No. 20125661 (2 pages).

Guerrero, L., et al., "Anaerobic hydrolysis and acidogenesis of wastewaters from food industries with high content of organic solids and protein," Water Research, Oct. 1999, vol. 33, Nr. 15, p. 3281-3290 (3 pages).

Communication of Acceptance issued by the Finnish Patent Office in connection with Finnish Priority Application No. 20125661 dated Jul. 11, 2013 (3 pages).

\* cited by examiner

METHOD FOR PROCESSING BIOLOGICAL MATERIAL

TECHNICAL FIELD

The present invention relates generally to new processes for producing ammonia and/or ammonium from organic raw materials by a process employing enzymes and microbial fermentation.

BACKGROUND OF THE INVENTION

Ammonia ($NH_3$) is one of the most produced chemical compounds in the world. The global production reached 131M metric tons in 2010 (US Geological Survey 2012). Most of the produced ammonia is used in chemical fertilizers to provide the nitrogen crops need for growing. Ammonia has also been used to produce plastics, synthetic fibers and resins, explosives, and numerous other chemical compounds.

At present, ammonia production is resource intensive and produces unwanted greenhouse gases. The most common industrial method for producing ammonia is the Haber-Bosch process, where hydrogen gas derived from methane (from natural gas) and nitrogen gas react in the presence of iron or ruthenium catalyst to form ammonia (Smil 2001). According to the chemical fertilizer industry, each metric ton of ammonia produced by this process releases two metric tons of $CO_2$, with an average recovery rate of some 38 percentage. Before being incorporated into a fertilizer product, the ammonia needs to be further reacted to produce known fertilizer compounds such as urea, ammonium nitrate, or ammonium phosphates. Nevertheless, despite the benefits of the Haber-Bosch process, there is a growing need to reduce the adverse environmental impact of fossil fuel based ammonia production and to find alternative methods for providing industrial quantities of ammonia and ammonium for fertilizer and other industrial applications.

The biochemical process of converting nitrogen containing biological material into ammonia is called ammonification (Gowariker 2009) or mineralization. The scientific literature on bacterial ammonification is based on the spontaneous production of ammonia obtained from test tube scale laboratory studies and have been reported from at least 24 bacterial genera, mainly derived from the digestive tracts of ruminants (Bladen et al. 1961 and citations therein; Vince & Burridge 1980; Chen & Russel 1988; Russel et al. 1988; Attwood et al. 1998; Rychlik & Russel 2000; Eschenlauer et al. 2002; Whitehead & Cotta 2004) including gram positive and negative bacteria (Whitehead & Cotta 2004).

Of the bacteria capable of ammonification, i.e., producing detectable amounts of $NH_4^+$, only approximately 20 strains belonging to genera such as *Clostridium, Eubacterium, Fusobacterium, Peptostreptococcus*, and *Pseudomonas*, originally isolated from ruminal and swine manure, have been reported to form ammonia ($NH_3$) at a rate of more than 40 nM (i.e., 681 mg $NH_3$/liter=about 730 mg $NH_4^+$/liter) per 24 h (Paster et al. 1993; Attwood et al. 1998; Russel et al. 1988; Chen & Russell 1988; Whitehead & Cotta 2004). These bacteria have been described as hyper ammonia-producing ("HAP;" e.g. Attwood et al. 1998; Whitehead & Cotta 2004) and as hyper ammonia-producing bacteria ("HAB") (Rychlik & Russel 2000).

The ammonia producing bacteria vary markedly in their preference of carbon source, as well as amino acids and peptides, of the substrate employed for ammonification (Vince & Burridge 1980; Rychlik & Russel 2000; Whitehead & Cotta 2004). The highest rate of production has been obtained in growth media containing peptides and amino acids digested from the milk protein casein (e.g., tryptone and casamino acids). With culture on intact casein, growth and production was detected from only 11 bacterial strains out of 40, including only a single strain with a high rate of production (47.6 mN $NH_3$ per 24 hrs; Whitehead & Cotta 2004). Depending on the bacterial strain, the presence of glucose or lactose increased, had no effect on, or decreased ammonia production (Vince & Burridge 1980; Eschenlauer et al. 2002; Whitehead & Cotta 2004).

Thus, there remains a longstanding need for an improved process for producing ammonia from organic raw materials utilizing microbial culture.

The citation of any reference herein should not be construed as an admission that such reference is available as "Prior Art" to the instant patent application.

SUMMARY OF THE INVENTION

Accordingly, what is now provided is a process for producing ammonia or ammonium from an organic material, the method including the steps of:

(a) contacting the organic material with at least one hydrolytic enzyme, in a medium, to produce a medium comprising hydrolyzed or partially hydrolyzed organic material suitable for microbial fermentation, (b) fermenting the medium comprising hydrolyzed or partially hydrolyzed organic material in the presence of at least one microorganism capable of ammonification, wherein the fermenting is under conditions, and for a sufficient period of time, to produce a fermentation product that comprises ammonia or ammonium;

wherein the organic material comprises nitrogenous compounds suitable for conversion to ammonia or ammonium.

In a preferred embodiment, the medium of (b) is enriched with a carbohydrate suitable for promoting microbial growth.

The at least one microorganism of the inventive process is selected from the group of microorganisms that are capable of anaerobic ammonification in the presence and absence of monosaccharides or disaccharides. These bacteria (e.g. some *Clostridium* species) may also be capable of fixing atmospheric nitrogen with nitrogenase enzyme expressed by those bacteria. In one embodiment, the at least one microorganism is a bacterium. Simply by way of example, the bacterium is an isolate from the genus of one or more of *Aeromonas, Citrobacter, Clostridium, Bacillus, Enterobacter, Enterococcus, Klebsiella, Pseudomonas* and *Staphylococcus*. Preferably, the bacterium is an isolate from the genus of one or more of *Aeromonas, Citrobacter, Clostridium* and *Enterococcus*. More preferably, the bacterium is an isolate that is a species of *Clostridium*, e.g., a species of *Clostridium perfringens, Clostridium beijerinckii* or *Clostridium butyricum* or combinations thereof. In one preferred embodiment, the bacterium is an isolate deposited as VTT-E-123272 and/or VTT-E-123273.

The at least one hydrolytic enzyme is, for example, an amylase, cellulose, protease, phytase and/or a combination thereof. Preferably, the hydrolytic enzyme is one or more of Alcalase®, *Aspergillus oryzae* acidic protease, *Aspergillus oryzae* acidic protease, *Aspergillus oryzae* alkaline protease, *Bacillus clausil* protease, *Bacillus lentus* protease, *Bacillus stearothemophilis* protease, *Bacillus subtillus* protease, bromelain, collagenase type 2, Flavourzyme® protease mix from *Aspergillus oryzae*, papain, pepsin, proteinase K, porcine pancrease trypsin and/or combinations thereof.

When the enzyme is Flavourzyme®, the Flavourzyme® is optionally present in the medium in a concentration ranging from about 300 mU through about 40,000 mU.

In a further embodiment, the process includes a step or steps of recovering ammonia or ammonium from the fermentation product, e.g., by mechanically separating the fermentation product or by precipitating the fermentation product. In one embodiment, the ammonia or ammonium is recovered by a process including:

(a) dehydrating the fermentation product to provide a dry fermentation product;

(b) collecting ammonia or ammonium-water or gas mixture released during the dehydrating step (a); and (c) recovering the ammonia or ammonium.

The inventive process optionally includes the following additional process steps:

(d) converting the recovered ammonia or ammonium to a unified form; and (e) recovering the unified form;

wherein the unified form is, for example, ammonium nitrate, ammonium sulphate, ammonium chloride, ammonium phosphate, diammonium phosphate and monoammonium phosphate and/or combinations thereof, or some other compound which is formed by ammonia reacting with nitric acid, sulfuric acid, hydrochloric acid, or phosphoric acid, or some other compound, respectively.

The nitrogenous compounds present in the organic material are, for example, amines or proteins. The organic material is any material suitable for the purpose, e.g., meat-and bone meal (MBM), slaughterhouse waste, whey, municipal waste, fish meal, food industry waste streams and combinations thereof. Food industry waste broadly include, for example, meals of meat-and-bone, fish, feathers, beet root, legumes, fruit, and sugar industry waste, to name but a few such materials.

The hydrolysis step of the inventive process is preferably conducted in a pH ranging from about pH 2 through about pH 14, and at a temperature ranging from about 20° C. through about 80° C. More preferably, the pH ranges from about pH 5.0 to about pH 9.0, and the temperature ranges from about 45° C. to about 65° C.

The fermenting step of the inventive process is preferably conducted in a pH ranging from about pH 2 through about pH 14, and at a temperature ranging from about 20° C. through about 70° C. More preferably, the pH ranges from about pH 6.0 to about pH 9.0, and the temperature ranges from about 30° C. to about 45° C.

The inventive process is preferably conducted in a medium that is an aqueous medium and wherein the organic material, e.g., MBM, is present in the medium in a concentration ranging from about 50 g/l to about 250 g/l.

In a further embodiment, the invention provides the fermentation product produced by the inventive process, e.g., compositions including ammonia or ammonium produced by the inventive process.

In a still further embodiment, the invention provides for bacteria isolates selected for the property of ammonification. Preferably, the bacterial isolates are from the genus of one or more of *Aeromonas, Citrobacter, Clostridium* and *Enterococcus*. More preferably, the bacterial isolates are a species of *Clostridium*, e.g., a species of *Clostridium perfringens, Clostridium beijerinckii* or *Clostridium butyricum* or a combination thereof. In one preferred embodiment, the bacterial isolate is deposited as VTT-E-123272 and/or VTT-E-123273.

DETAILED DESCRIPTION OF THE INVENTION

Figure 1:
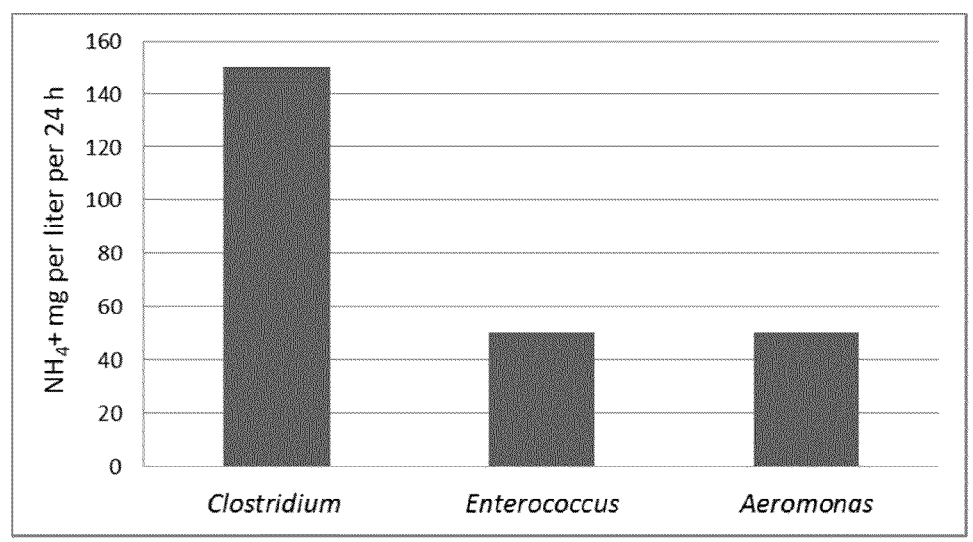
FIG. 1. Illustrates bacterial ammonium ($NH_4$) production from 179 g/l of non-hydrolyzed MBM and of 0.2 % glucose as described by Example 1. The $NH_4^+$ detected from the culture medium without bacteria (background) was 150 mg/l and has been subtracted from production values in the presence of fermenting bacteria. No bacterial ammonium ($NH_4^+$) production was measured from non-hydrolyzed meat-and-bone meal medium when bacteria were incubated without glucose.

The present invention provides an improved process for producing ammonia or ammonium from an organic material.

Broadly, the inventive process includes, for example, the following steps for converting an organic material to ammonia and/or ammonium.

Step 1: Hydrolyzing organic material that includes nitrogenous compounds using a suitable enzyme.

Step 2: Fermenting the hydrolyzed organic material by inoculating one or more ammonification microorganisms into the hydrolyzed organic material and culturing the inoculated organic material under suitable conditions and for a sufficient time period.

Step 3: Collecting/recovering ammonia and/or ammonium from the fermented organic material.

The method utilizes nitrogen and amine rich waste sources, such as meat-and-bone meal (MBM), and ammonia producing bacteria. The ammonia production can be further enhanced by supplying the ammonia producing bacteria with a carbohydrate source such as glucose, molasses and or waste vegetables, fruit, root vegetables, or their peels.

In order to more clearly appreciate the invention, the following terms are defined. The terms listed below, unless otherwise indicated, will be used and are intended to be defined as indicated. Definitions for other terms can occur throughout the specification. It is intended that all singular terms also encompass the plural, active tense and past tense forms of a term, unless otherwise indicated.

The term "nitrogenous compounds" refers to nitrogen compounds suitable for conversion to ammonia or ammonium by the process of the invention, e.g., organic nitrogen, including amines, proteins and the like.

The term "ammonia" refers to the compound $NH_3$ found in gaseous form or dissolved in a non-ionized form in a medium e.g., an aqueous medium. The term "ammonium" refers to the ion which is the ionic form of $NH_3$ found in e.g., aqueous solution. In aqueous solution, ammonium and ammonia occur in an equilibrium that is dependent on temperature and pH, e.g. the higher the temperature and the pH, the greater the proportion that is in the form of ammonia. For this reason, reference to "ammonia" herein with regard to the inventive process and/or ammonification microorganisms and products thereof should be understood to include reference to both $NH_3$ and $NH_4^+$ forms of this compound, unless otherwise indicated. For example, discussion of ammonification microorganisms as "ammonia producing" or "ammonium producing" is understood to include production of $NH_3$ and/or $NH_4^+$ according to the $NH_3/NH_4^+$ equilibrium found in the particular medium.

The term "unified form," as used herein in the context of recovery of ammonium and ammonia from the fermentation products, refers to conversion of ammonium ions into another chemical form such as nonionic ammonia ($NH_3$) and/or any art known nitrogen containing compound, e.g., a compound which is formed by ammonia reacting with nitric acid, sulfuric acid, hydrochloric acid, or phosphoric acid, or some other compound, respectively.

Microorganisms for Ammonification

Ammonia producing microorganisms according to the invention include any microorganisms capable of ammonification or mineralization when cultured on substrates or in a medium that includes nitrogenous compounds. Such microorganisms include, for example, bacteria and fungi that are able to convert organic nitrogen into ammonia or ammonium. In particular embodiments, bacteria belonging to the taxonomic genera *Aeromonas*, *Citrobacter*, *Clostridium*, *Enterobacter*, *Enterococcus*, *Klebsiella*, *Pseudomonas*, or *Staphylococcus* are preferred. Useful microorganisms according to the invention are isolated from sources such as, without limitation, animal feces. Isolated strains employed in the inventive method were isolated by the following process.

Bacterial strains were isolated from sludge samples taken from a water treatment plant and from animal feces. The samples were first diluted and cultivated on LB agar plates (10 g/l tryptone, 5 g/l yeast extract, 5 g/l NaCl, 15 g/l agar). Single colonies were inoculated repeatedly on SE (selective medium) (3 g/l yeast extract, 10.2 g/l tryptone, 10 g/l amino acids, 5 g/l NaCl, 2.6 g/l $K_2HPO_4$, 15.1 g/l agar) and cultivated as pure cultures.

The ammonium production of the isolated strains was screened in BHI-medium (Brain-Heart-Infusion Broth, Oxoid) or in a semi-defined medium used by Whitehead & Cotta (2004). The strains were first cultivated in BHI-medium at +37° C. or RT for 16-24 h. From these, 70 µl of the culture was inoculated to 10 ml of fresh BHI or semi-defined medium. Ammonium production was measured after 24 h anaerobic cultivation at +37° C. with ammonium test strips (Meckoquant, Merck) using the manufacturer's instructions. For some of the strains, ammonium production was also measured after 6 h cultivation.

Approximately 700 different bacterial strains were screened. Screening results were studied and the best ammonium producing bacteria were chosen. Preferred selected strains have been deposited under the terms of the Budapest Treaty in the VTT Culture Collection, P.O. Box 1000 (Tietotie 2) FI-02044 VTT, Finland and given deposit numbers, as follows.

The first selected strain is identified herein as "Strain 385" that belongs to *Clostridium* genus, *beijerinckii* or *butyricum* species, and is deposited as VTT E-123273 (VTT Culture Collection, Finland). The genus was determined based on its 16S rRNA nucleotide sequence. The commercially available API-test system (of bioMerieux, Inc., Hazelwood, Mo., USA) for bacterial identification was used to determine the species. Note: Used API-test provides information that the species is either *beijerinckii* or *butyricum* i.e. probability is 50:50.

The second selected strain is identified herein as "Strain 393" that belongs to *Clostridium* genus, *perfringens* species, and is deposited as VTT E-123272 (VTT Culture Collection, Finland). The genus was determined based on its 16S rRNA nucleotide sequence. The commercially available API-test system (of bioMerieux, Inc., Hazelwood, Mo., USA) for bacterial identification was used to determine the species).

In considering the source of ammonia or ammonium produced by microorganisms, the artisan will appreciate that some bacteria express a nitrogenase enzyme that intracellularly converts $N_2$ gas into ammonium. For example, certain *Clostridium* species fix atmospheric nitrogen. Thus, ammonification is not the only mechanism by which microorganisms according to the invention may produce ammonia or ammonium during the fermenting step of the process.

Hydrolytic Enzymes

The term "hydrolytic enzymes" as used herein refers to any enzyme that is able to catalyze hydrolysis of a chemical bond and that can be used in the inventive process. Preferred examples of hydrolytic enzymes are enzymes that catalyze the hydrolysis of proteins, peptides, nucleic acids, starch, fats, phosphate esters, and other macromolecular substances. Preferred hydrolytic enzymes comprise serine and other proteases and peptidases (such as alkalases, collagenases, keratinases, and pepsin). For example, proteinaceous substrates can be hydrolyzed into peptides and amino acids which can be utilized by fermenting bacteria.

Other hydrolytic enzymes to be used in certain embodiments of the invention include amylases, e.g., α-amylases, β-amylases and glycoamylases, cellulases, e.g., endoglucanases, cellobiohydrolases and β-glucosidases, and hemicellulases, e.g., xylanases and mannanases, and side-chain cleaving enzymes, e.g., α-glucuronidases, acetyl xylan esterases, α-arabinofuranosidases, and α-galactosidases to hydrolyze high molecular weight polymers into monomeric hexose and pentose sugars, which may be fermented by the microorganisms.

Different enzyme mixtures for hydrolyzing proteins and starch, cellulose, and hemicellulose polymers, depending on the material to be hydrolyzed, are art known and commercially available. Preferably, the enzymes employed in the inventive process include, for example, Alcalase®, *Aspergillus oryzae* acidic protease, *Aspergillus oryzae* alkaline protease, *Bacillus clausil* protease, *Bacillus lentus* protease, *Bacillus stearothemophilis* protease, *Bacillus subtillus* protease, bromelain, collagenase type 2, Flavourzyme® protease mix from *Aspergillus oryzae*, papain, pepsin, proteinase K, porcine pancrease trypsin and combinations thereof.

Organic Material

The term "organic raw material" or "organic material" as used herein refers to any carbon and nitrogen rich material of biological origin which can be used in the processes described herein as a substrate for mineralization by ammonia producing microorganisms. Examples of such organic material include amine containing material, e.g., proteinaceous material such as, e.g., meat-and bone meal (MBM), slaughterhouse waste, whey, municipal waste, fish meal, food industry waste streams, e.g., animal and plant by-products including, but not limited to, the meal of meat-and-bone, fish, and feathers, as well as beet root, legumes, fruit, and sugar industry waste.

The term "MBM" "meat-and-bone meal" is employed herein as defined by European Union Commission Regulation No. 142/2011 "meat-and-bone meal means animal protein derived from the processing of Category 1 or Category 2 materials in accordance with one of the processing methods set out in Chapter III of Annex IV".

Based on the Directive:

Category 1 consists of material with the highest risk of infectious disease such as Transmissible Spongiform Encephalopathy (TSE). It encompasses animals confirmed or suspected to be infected by a TSE, as well as test animals, animals suspected of being infected by a zoonotic disease, and by-products contaminated by (illegal) substances or environmental contaminants. Bovine, ovine, and caprine TSE risk slaughter material (crania, vertebrae, intestines, and digestive tubes) also falls into category 1.

Category 2 consists of materials associated with a lower infection risk. Category 2 encompasses manure, guano and digestive tract contents, animals that died not by being slaughtered for human consumption but of a disease or disease control measures, animal by-products containing residues of authorized substances or contaminants exceeding the permitted levels of Directive 96/23/EC, as well as animal by-products other than category 1 and 3 materials.

Category 3 represents the lowest disease risk. It consists of animal carcasses and body parts not diseased, but not intended for human consumption, for commercial or other reasons, as well as parts such as bones, hair, fur, feathers, wool, hides and skins, horns and feet, adipose tissue, placentae, heads of poultry, and pig bristles. Category 3 also covers eggs, milk, and waste from milk processing. All material must derive from non-diseased animals including aquatic animals and TSE negative ruminants.

The MBM used in the examples hereinbelow was of category 3.

Meat-and-bone meal is prepared from animal protein derived from animal carcasses, parts and by-products. It is produced from rendering the waste parts of mixed species that are not suitable, or not used, for human consumption. These include feathers, hair, wool, horn, hooves, skin etc. in addition to meat and bone. The composition of the starting material used for MBM production varies between batches and production plants, leading to differences in MBM properties such as crude protein, ash, calcium, and phosphorus content.

Rendering is the process whereby the material is processed to separate protein from fat. Annex IV of Commission Regulation (EU) No 142/2011 describes processing methods for various categories, according to which MBM is produced. Typically, the category 1 and 2 animal-derived material reduced in size to less than 50 mm is heated at 133° C. for at least 20 minutes at a pressure of at least 3 bar (=pressure sterilization). Alternative methods are can be used for various particle sizes as well as category 3 materials. After heating, the fat is extracted by compression, and the remaining material ground to particle size of less than 2 mm.

The rendering process for the MBM included the steps of removing water and drying in 180 degrees of Celsius in 8 bar pressure (of particles with size of less than <50 mm), followed by breaking the particle size to less than 30 mm. This was followed by sterilization at 133 Celsius, 3 bar pressure, for 20 minutes, and final drying to reduce the water content to approximately 2%-4% of total weight. The final drying step was followed by separation of fats and solids by pressing. The resulting MBM was further cooled and milled.

Fermentation Conditions

Fermentation refers to a process for growing bacteria under anaerobic conditions. In the examples herein, the fermenting process was conducted in 10-15 ml glass roll tubes, typically at 37 Celsius, for a given time, e.g., 24 hours.

Alternatively, the fermenting process is optionally conducted with an in-place sterilizable fermenter system, e.g., Biostat C plus (Sartorius-Stedim, Germany) that has from 7 to 30 liters of working volume and an MFCS/win (SCADA) software system configured for cell culture applications.

The fermenting process is also optionally conducted in industrial sized fermenting equipment purposed for mass production. Exemplary pH is in the range of 7-7.5.

Recovery of Produced Ammonia

Post processing refers to the process of collecting (recovering) ammonia from the liquid for example, as ammonium or ammonia. The produced ammonia can be collected from the bacterial culture as gas ($NH_3$) and can be, for example, dissolved into an acid solution with, e.g., an ammonia stripping method (Guštin & Marinšek-Logar, 2011) in which ammonium is converted to ammonia by high pH, ranging for example from pH 9 to pH12, high temperature (e.g. 60° C.) and then the $NH_3$ gas is contacted, with the help of aeration, with nitric acid ($HNO_3$). Ammonium nitrate ($NH_4NO_3$) is formed by the reaction of ammonia and nitric acid: $NH_3 + HNO_3 \rightarrow NH_4NO_3$. Other acids that may be reacted with ammonia include, e.g.: sulphuric acid ($H_2SO_4$) in a reaction of $2NH_3 + H_2SO_4 \rightarrow (NH_4)_2SO_4$ (ammonium sulphate), hydrochloric acid (HCl) in a reaction of $NH_3 + HCl \rightarrow NH_4Cl$ (ammonium chloride), and phosphoric acid ($H_3PO_4$) in three alternative reactions: $3\ NH_3 + H_3PO_4 \rightarrow (NH_4)_3PO_4$ (ammonium phosphate), $2\ NH_3 + H_3PO_4 \rightarrow (NH_4)_2HPO_4$ (diammonium phosphate, DAP) or $NH_3 + H_3PO_4 \rightarrow NH_4H_2PO_4$ (monoammonium phosphate, MAP). Finally, the solution can be concentrated and or dehydrated. Alternatively, ammonia can be collected as ammonium ions ($NH_4^+$) using one of the precipitation methods that results in e.g., struvite ($MgNH_4PO_4.6H_2O$) in a reaction of $Mg^{2+}+NH_4^++PO_4^{3-}+6H_2O \leftrightarrow MgNH_4PO_4.6H_2O$ (Schulze-Rettmer et al. 2001; Nelson et al. 2003) or with a mechanical method such as size based nano-membrane filtration.

mass. The MBM also has other important nutrients, such as phosphorous (typically 4-6%) and calcium (7-12%). MBM used in the examples herein was analyzed by MTT Agrifood Research Finland to determine its composition. MBM of EU Category III was employed, as defined hereinabove. Table 1 below summarizes the MBM elemental analysis.

TABLE 1

| Dry matter | N | Ca | Mg | P | S | K | Na | Fe | Cu | Zn | Mn |
|---|---|---|---|---|---|---|---|---|---|---|---|
| 96.6 | 8.42 | 10.80 | 0.21 | 5.34 | 0.49 | 0.32 | 0.49 | 0.027 | 0.001 | 0.011 | 0.0001 |

The artisan will appreciate that the design of the entire ammonia production process depends on whether optimal production requires a high or low percentage of ammonia present in the final fermentation medium. If optimization of the process requires producing a medium with a high concentration of ammonia per liter, a high concentration of organic material, such as MBM, in the fermentation medium is preferred. If the desired optimization parameter is yield (i.e., how much of the organic material is converted to ammonia) a lower concentration of organic material in the fermentation medium is preferred. In some ammonium recovery processes it might be preferable to select a value with an intermediate concentration.

For example if the resulting liquid, with ammonia, is post processed by a process called "stripping" the quantity of ammonia per liter at the end of fermentation should be high, such as from 7 to 10 g/liter of liquid. Alternatively if the material cost (i.e., the cost of raw materials) is high, then it might be preferable to aim for a high yield of ammonia, such as more than 30% of all nitrogen harvested.

Figure 6:
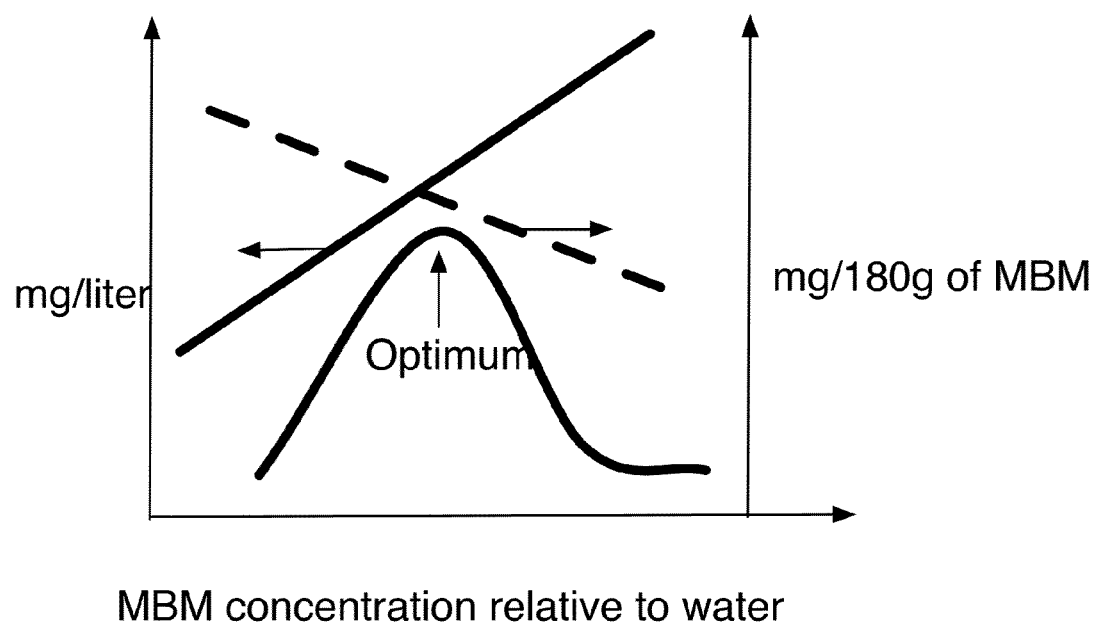
FIG. 6. Illustrates a method for optimizing the production process. The dashed line indicates yield (i.e. mg/180 g of MEM), for example, what percentage is converted to ammonium. The solid line indicates the concentration of ammonia in the liquid.

FIG. 6 illustrates a method for optimizing the production process. The dashed line indicates yield (i.e. mg/180 g of MBM) for example what percentage is converted to ammonium. The solid line indicates the concentration of ammonia in the liquid. Since, with some bacteria, yield decreases at the same time as concentration increases there is optimum process that depends, for example, on the raw material cost per weight unit and on the cost of the ammonium collection cost per processed amount of liquid.

In addition or alternatively to recovering $NH_3$ as a gas, the liquid containing $NH_4^+$ and/or $NH_3$ can be used as a fertilizer/nutrients source as it is in a concentrated form. In addition or alternatively solid materials from the fermentation processes can be used as fertilizers.

EXAMPLES

The following examples represent processes and compounds of the present invention. While the present invention has been described with specificity in accordance with certain embodiments of the present invention, the following examples further serve only to exemplify and illustrate the present invention and are not intended to limit or restrict the effective scope of the present invention.

Example 1

Bacterial Ammonification in Liquid Medium with Meat-and-Bone Meal (MBM) and Glucose Sterilized and milled MBM generally has a total protein concentration of approximately 40-60% (for example 52%) which corresponds to about 8% of the nitrogen of the MBM Bacterial isolates from different origins and belonging to three different bacterial genera according to their 16S rRNA gene sequence (*Aeromonas, Clostridium*, and *Enterococcus*), were used in the examples. In particular, the *Clostridium* isolate of Strain 393 was used in Example 1 for the *Clostridium* species.

Bacteria were grown anaerobically, as two replicates in 10 ml loose cap (LC) roll tubes, in 5 ml of an autoclaved liquid medium [179 g of MBM per liter, 0.2% of D(+)-Glucose (Merck), RO water, pH 7.4] at +37° C. for 24 hrs from which 100 µl of the culture was added to anaerobic Hungate culture tubes (Hungate 1969) containing 14 ml of the same autoclaved MBM medium. The controls contained media without bacteria. All of these were incubated again at +37° C. for 24 hrs.

1 ml of each sample was collected and centrifuged at 16,000× g (Eppendorf) for one minute and 500 µl of the supernatant was used for ammonium detection. The ammonium was measured with Ammonium Test (colorimetric with test strips; Merck) according to the manufacturer's instructions. The same experiment was also conducted with bacteria from genera *Aeromonas* and *Clostridium* with MBM medium lacking glucose. In this experiment without glucose, no ammonium could be detected.

Results. The bacterial cultures belonging to three different taxonomic genera (*Aeromonas, Clostridium*, and *Enterococcus*) were tested and shown to be capable of mineralizing protein-rich meat-and-bone meal (MBM) and producing ammonia in the presence of glucose. Without added glucose, the bacteria produced no detectable amounts of ammonia. This is confirmed by FIG. 1. In FIG. 1, bacterial ammonium ($NH_4^+$) production from 179 g/l of non-hydrolyzed MBM and of 0.2% glucose with *Clostridium, Enterococcus*, and *Aeromonas*, respectively, it illustrated. The $NH_4^+$ detected from the culture medium without bacteria (background) was 150 mg/l and has been subtracted from production values in the presence of fermenting bacterial. No bacterial ammonium ($NH_4^+$) production was measured from non-hydrolyzed meat-and-bone meal medium when bacteria were incubated without glucose.

The *Aeromonas* and *Enterococcus* species were obtained from waste water and animal facets respectively and clearly provided only about one third of the ammonium production capacity of the *Clostridium* isolates of Strain 393 under the conditions of this example.

Example 2

Positive Effect of Various Carbohydrate Sources on Bacterial Ammonia Production on Non-Hydrolyzed MBM The carbohydrate sources used in this study were apple peals, molasses, and D(+)glucose (Merck). The concentration of reducing sugars of the apple peals and the molasses was measured by the DNS-method (dinitrosalicylic acid; Miller 1959) as follows. Apple peal crush that was boiled in a small amount of water, and molasses-water mix, was sterile filtered and further diluted to 1:10 and 1:100. Samples, including standard dilution series, were incubated with 600 µl of DNS solution (1% dinitrosalicylic acid, 0.2% phenol, 0.05% Na-sulphate) at 90° C. fur 10 min. 200 µl of 40% KNa tartrate solution was added to terminate the color reaction. Absorbance was measured at 575 nm by using a spectrophotometric plate reader Synergy H1 Hybrid Reader (Biotek). Results were calculated from the standard curve made with dilution series of D(+)-Glucose. Based on the results the concentration of reducing sugars for each sample in the experiment was chosen to be approximately 0.2%.

Figure 2:
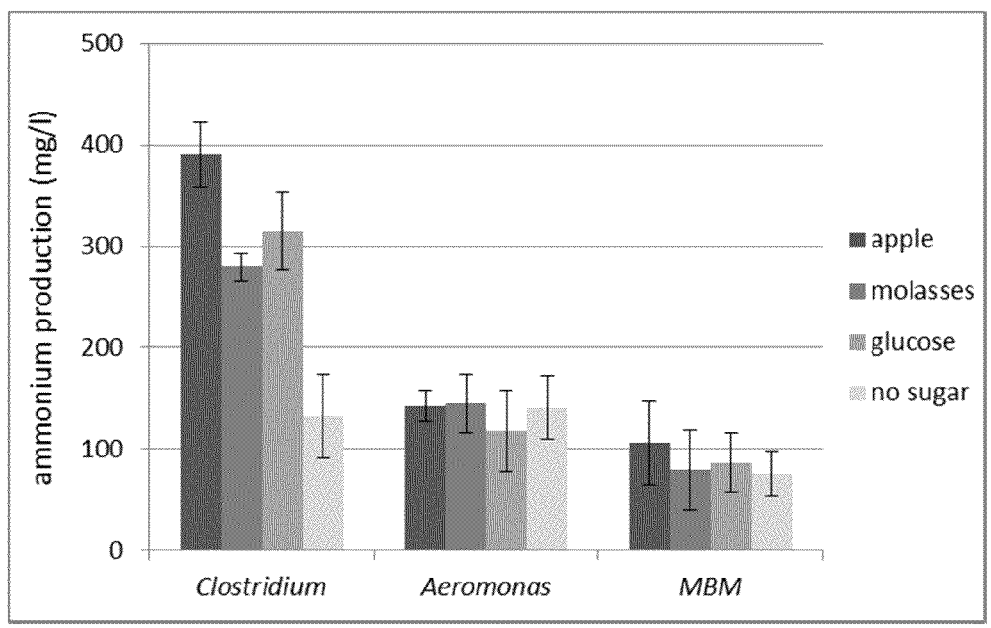
FIG. 2. Illustrates the effect of an added carbon source on bacterial ammonification on non-hydrolyzed MBM as described by Example 2. The final concentration of added reducing sugars from apple peal and potato concentrates, molasses, and glucose was approximately 0.2%. Results were from two biological replicates with 3 technical replicates in each. An 18-hr incubation with non-hydrolyzed MBM and an added carbohydrate enabled bacterial ammonification.

Bacteria were incubated with and without the carbohydrate sources as in Example 4 (hereinbelow) except that in the instant example, the MBM medium lacked glucose and was not subjected to a hydrolyzation step. Ammonium production by bacteria incubated in non-hydrolyzed MBM supplied with a fruit concentrate or molasses indicate that some bacteria including *Clostridium* are also able to use sugars other than purified glucose as their carbon source (Table 2; FIG. 2). In particular *Clostridium* isolate of Strain 393 was used in the example 2.

TABLE 2

Ammonium production in non-hydrolyzed MBM with different sugars (0.2%) added in a18-hr fermentation. Results are from 2 experiments with 3 technical sample replicates in each.

| | apple $NH_4^+$ mg/l | molasses $NH_4^+$ mg/l | glucose $NH_4^+$ mg/l | no sugar $NH_4^+$ mg/l |
|---|---|---|---|---|
| *Clostridium* | 390 ± 32 | 279 ± 14 | 315 ± 38 | 133 ± 41 |
| *Aeromonas* | 142 ± 15 | 146 ± 29 | 118 ± 40 | 142 ± 32 |
| No bacteria | 106 ± 41 | 79 ± 40 | 87 ± 29 | 76 ± 22 |

Example 3

Effect of the Proteolytic Alcalase® Enzyme on MBM

MBM medium [179 g of MBM per liter RO water, 0.2% of D(+)-Glucose (Merck), 50 mM MOPS, pH 7.5] was hydrolyzed with six different concentrations (up to 769 mU/ml) of proteolytic Alcalase® enzyme (CLEA Technologies) at 50° C. for 4 hrs. The proteolytic enzyme was inactivated by incubation with 50 µl of 20% SDS per 1.3 ml reaction volume, at 75° C. for 15 min. The proteins were extracted from the MBM samples by boiling in alkaline SDS buffer [5% SDS, 50 mM Tris (pH 8), 0.15 M NaCl, 0.1 mM EDTA, 1 mM MgCl2, and 1 mM DTT] as described by Chourey et al. (2010).

Figure 3A:
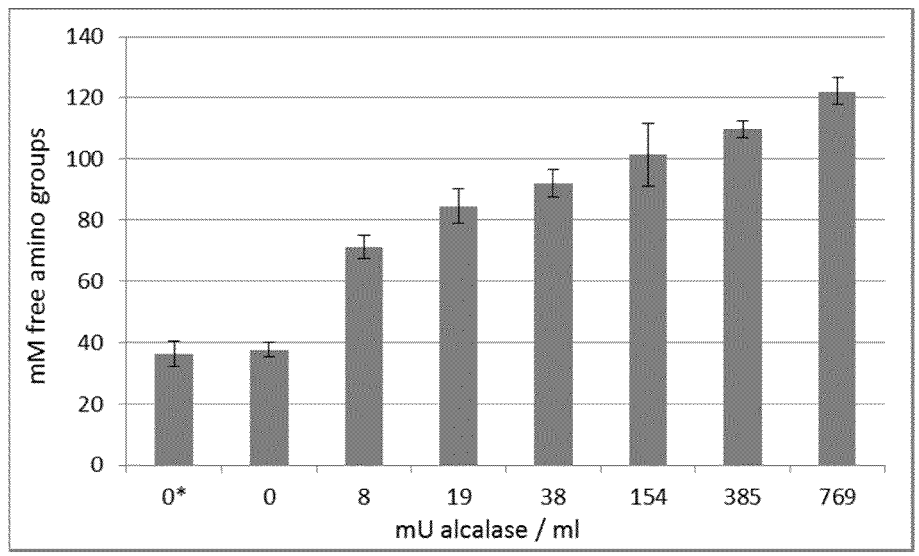
FIG. 3A. Illustrates the effect of enzymatic protein hydrolyzation MBM as described by Example 3. The MBM medium was hydrolyzed with six different concentrations (x-axis) of proteolytic Alcalase® enzyme (CLEA Technologies) at 50° C. for 4 hrs. The amount of free amino groups measured from MBM medium refer to the degree of MBM protein and peptide hydrolyzation.
Figure 3B:
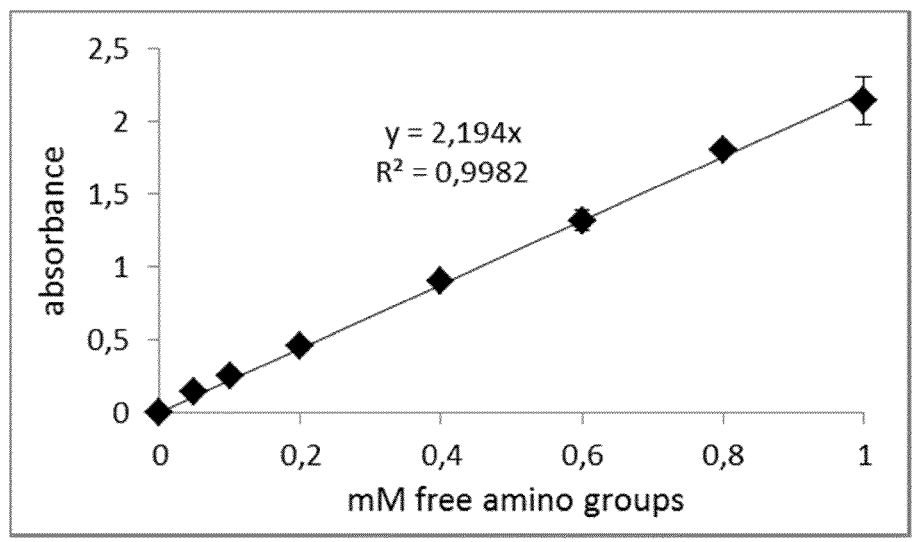
FIG. 3B. Illustrates the effect of enzymatic protein hydrolyzation of MBM as described by Example 3. In 3B, the amounts of free amino groups were calculated with a help of a standard curve based on a glycine dilution series (a glycine molecule contains a single amino group). The amount of free amino groups in MBM medium increased significantly after enzymatic treatment. Furthermore, instead of a 4 hr incubation, a 24 hr incubation with 8 mUnit of Alcalase® per ml of MBM medium increased the degree of MBM hydrolyzation over 30% (data not shown).

The hydrolyzation of MBM was verified by quantifying free amino groups from the MBM medium, with and without protease treatment, using TNBS-method (trinitrobenzene sulfonic acid; Navarrete & Garda-Carrêno 2002). A standard dilution series was made with glycine and treated similarly as the MBM containing samples. 100 µl of the hydrolyzed MBM medium, controls, and standards were each mixed with 900 µl of 0.1 M Na-bicarbonate buffer (pH 8.5), then 100 µl of those were mixed with 50 µl of 0.1% (w/v) of TNBS reagent [picrylsulfonic acid 5% (w/v) in $H_2O$ (Sigma) and Na-bicarbonate buffer pH 8.5] in wells of a clear 96-well plate and incubated in the dark at 37° C. for 2 hrs. The reaction was terminated by adding 50 µl of 10% SDS and 25 µl of 1 M HCl. The absorbance of cooled samples was measured at 335 nm by using a spectrophotometric plate reader Synergy H1 Hybrid Reader (Biotek). Results (FIG. 3A) were calculated from the standard curve made with the glycine dilution series (FIG. 3B).

The free amino groups in MBM medium increased significantly after enzymatic treatment. With 19 mUnit of Alcalase® per ml of MBM medium, hydrolyzation of MBM was doubled compared to an untreated sample and with 769 mUnit of Alcalase® per ml of MBM medium, hydrolyzation of MBM was tripled (FIG. 3A). Furthermore instead of a 4 hr incubation, a 24 hr incubation with 8 mUnit of Alcalase® per ml of MBM medium increased the degree of MBM hydrolyzation over 30% (data not shown).

Example 4

Positive Effect of Protein Hydrolyzation of MBM by Alcalase® on Bacterial Mineralization MBM medium [179 g of MBM per liter RO water, 0.2% of D(+)-Glucose (Merck), 50 mM MOPS, pH 7.5] was hydrolyzed with 385 mU of Alcalase® enzyme (CLEA Technologies) per ml at 50° C. for 4 hrs. The enzyme was inactivated in the MBM medium by boiling for 5 min. In Example 3 this concentration of Alcalase® enzyme (CLEA Technologies) was shown to cause significant proteolysis of MBM (see FIG. 3A of Example 3). The extent of MBM hydrolyzation was quantified by using the TNBS-method (Navarrete & Garda-Carreno 2002) described in Example 3.

Figure 4A:
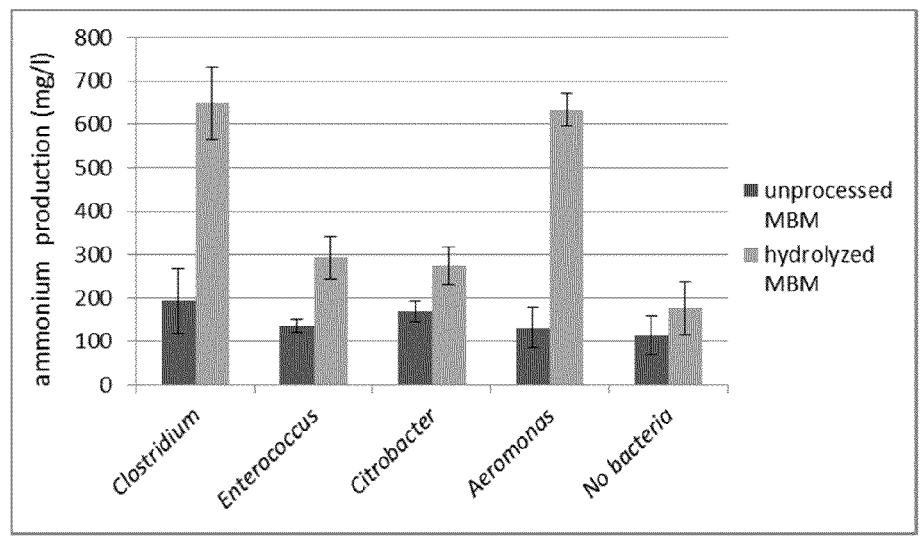
FIG. 4A. illustrates the effect of protein hydrolyzation of MBM on bacterial ammonification as described by Example 4. MBM medium was hydrolyzed with proteolytic Alcalase® enzyme (CLEA Technologies) at 50° C. for 4 hrs prior to bacterial inoculation (*Aeromonas, Citrobacter, Clostridium,* and *Enterococcus*). The control was untreated MBM medium with bacteria. Error bars refer to standard deviation of 2-4 experiments with three technical sample replicates.

Bacterial isolates from four different genera (*Aeromonas, Citrobacter, Clostridium*, and *Enterococcus*) were cultivated anaerobically (using Anaerocult A, Merck) in autoclaved Brain-Heart-Infusion (BHI) Broth (Oxoid) [37 g BHI per liter of water purified by reverse osmosis ("RO")] at 37° C. for 16-24 hrs. From these, 70 µl of the culture was inoculated into 10 ml of hydrolyzed or non-hydrolyzed liquid MBM medium [179 g MBM, 0.2% D(+)Glucose (Merck), RO water, 50 mM MOPS, pH 7.5] and incubated at 37° C. for 18 hrs. In addition, bacterial isolates of *Aeromonas* and *Clostridium* were incubated with hydrolyzed MBM and with various sugar sources, and with no sugar (see methods in Example 2, hereinabove). Ammonium ($NH_4^+$) was measured by using a quantitative, enzymatic determination kit for ammonia (Ammonia Assay Kit AA0100; Sigma-Aldrich) for biological samples, according to manufacturer's instructions. Before measuring, samples were diluted with Phosphate Buffer Solution, Medicago (0.14 M NaCl, 0.003 M KCl, 0.01 M Phosphate buffer, pH 7.4) as 1:80 and the controls without bacteria as 1:30. Ammonia Standard Solution (10 µg/ml) was diluted to contain 2, 4, 6, and 8 µg/ml of ammonia to act as a standard curve. The absorbance was measured at 340 nm by using a spectrophotometer Synergy H1 Hybrid Reader (Biotek). Hydrolyzed MBM medium resulted in even 3 to 5 times more of bacterial $NH_4^+$ production (about 649 mg and 633 mg per liter per 18 hrs) than non-hydrolyzed (i.e. unprocessed) that resulted in about 192 mg and 130 mg of $NH_4^+$ per 18 hrs from *Clostridium* and *Aeromonas*, respectively (Table 3; FIG. 4A). The enzymatic treatment of MBM prior to bacterial fermentation significantly increased bacterial ammonium production. The magnitude of the effect was dependent on the bacteria (Table 3; FIG. 4A).

TABLE 3

Ammonium (NH4+) production with bacteria in unprocessed and hydrolyzed MBM in a 18 hr fermentation. Results are from 2-4 experiments with 3 technical replicates in each.

|  | unprocessed MBM $NH_4^+$ mg/l | hydrolyzed MBM $NH_4^+$ mg/l |
|---|---|---|
| Clostridium | 192 ± 75 | 649 ± 83 |
| Enterococcus | 135 ± 15 | 292 ± 49 |
| Citrobacter | 169 ± 23 | 273 ± 44 |
| Aeromonas | 130 ± 46 | 633 ± 39 |
| No bacteria | 113 ± 45 | 175 ± 62 |

Figure 4B:
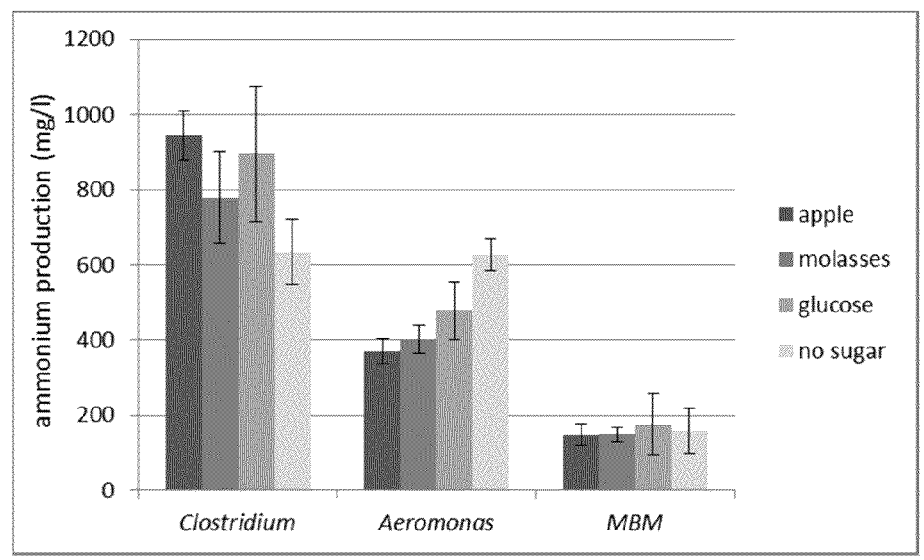
FIG. 4B. Illustrates the effect of protein hydrolyzation of MBM on bacterial ammonification as described by Example 4. Ammonium was produced with hydrolyzed MBM with and without various carbon sources for 18 hrs. Error bars refer to standard deviation of 3 experiments with 3 technical sample replicates in each. Hydrolyzation of MBM prior bacteria inoculation (*Clostridium* and *Aeromonas*) resulted in effective ammonia production. Moreover, the incubation with non-hydrolyzed MBM and a carbon source resulted in less ammonium than incubation with hydrolyzed MBM without an added carbon source (compare to FIG. 2.).

While bacteria from genera *Aeromonas* and *Clostridium* produced ammonium from non-hydrolyzed MBM only in small amounts, and produced no ammonium from non-hydrolyzed MBM without added glucose (see Examples 2 and 3, hereinabove), the same bacteria from genera *Clostridium* and *Aeromonas* did not require addition of carbohydrate for their ammonia production when the MBM was enzymatically hydrolyzed before fermentation (see Table 3; FIG. 4B) even though apple peal crush, molasses, and glucose increased ammonia production in *Clostridium* (Table 4; FIG. 4B).

TABLE 4

Ammonium production in hydrolyzed MBM with different sugars (with reducing sugars added in a concentration of 0.2%) for an 18 hr fermentation. Results are from 3 experiments with 3 technical replicates in each.

|  | apple $NH_4^+$ mg/l | molasses $NH_4^+$ mg/l | glucose $NH_4^+$ mg/l | no sugar $NH_4^+$ mg/l |
|---|---|---|---|---|
| Clostridium | 944 ± 64 | 779 ± 120 | 895 ± 179 | 634 ± 86 |
| Aeromonas | 371 ± 33 | 403 ± 38 | 479 ± 77 | 627 ± 43 |
| No bacteria | 148 ± 30 | 150 ± 19 | 176 ± 81 | 158 ± 62 |

In conclusion, a treatment of MBM with a proteolytic enzyme prior to bacterial fermentation significantly increases bacterial ammonia production. Furthermore, the treatment obviates the necessity of an added carbohydrate in some cases. Carbohydrate addition has an enhancing co-effect with hydrolyzation on bacterial ammonia production with *Clostridium* and in particular with the *Clostridium* isolate of Strain 393.

Example 5

Positive Effect of Protein Hydrolyzation of MBM by a Range of Enzymes on Bacterial Mineralization The benefits of pre-hydrolyzing MBM was tested using number of different commercial enzymes. MBM medium was prepared as follows: 180 g MBM, 2 g glucose, and 1 liter water were mixed and autoclaved at 121° C. for 15 min. Aliquots of 1.3 ml of MBM medium were hydrolyzed with different concentrations of the enzymes for 24 h. The enzymes were added in medium in volumes 1-100 µl. Optimal hydrolyzation temperature and pH were chosen according to the recommendations of the manufacturer or by the information presented in literature, and the specific hydrolyzation conditions for each enzyme are shown in Table 5, hereinbelow.

The MBM medium was buffered with 50 mM MOPS (4-morpholinepropanesulfonic acid), Tris, glycine, or acetate buffer as shown in Table 5. In addition, in the hydrolyzation reactions with collagenase, proteinase K, and trypsin, 5 mM CaCl was added in the MBM medium. The hydrolyzation reactions were stopped by adding 50 µl 20% of SDS to the samples and heating the samples at 75° C. for 15 min. The proteins were extracted from the MBM samples by boiling in an alkaline SDS buffer [5% SDS, 50 mM Tris (pH 8), 0.15 M NaCl, 0.1 mM EDTA, 1 mM MgCl2, and 1 mM DTT] as described by Chourey et al. (2010).

The degree of hydrolyzation was defined by quantifying free amino groups in the protein samples of enzymatically treated and untreated MBM samples using TNSB method (trinitrobenzene sulfonic acid; Navarrete del Toro & Garcia-Carreño 2002). A standard dilution series was prepared with glycine and treated similarly as the MBM containing samples.

A hundred microliter of the hydrolyzed MBM medium was mixed with 900 µl of 0.1 M Na-bicarbonate buffer (pH 8.5), then 100 µl of those were mixed with 50 µl of 0.1% (w/v) of TNBS reagent [picrylsulfonic acid 5% (w/v) in H2O (Sigma) and Na-bicarbonate buffer pH 8.5] in the wells of a clear 96-well plate and incubated in the dark at 37° C. for 2 hrs. In addition control samples (MBM without hydrolyzation), and standards dilution series were each mixed in the same manner as the MBM medium. The reaction was terminated by adding 50 µl of 10% SDS and 25 µl of 1 M HCl. The absorbance of the cooled samples was measured at 335 nm by using a spectrophotometric plate reader Synergy H1 Hybrid Reader (Biotek). The results were calculated from the standard curve made with dilution series of glycine.

Results

The hydrolyzation results of all the enzymes tested are shown in Table 5.

TABLE 5

Hydrolyzation of MBM medium using 14 different enzymes: hydrolyzation condition, range of tested enzyme concentrations, and the increase of free amino groups (mM) in the MBM medium after enzymatic treatment. The concentration of free amino groups in the MBM medium before the enzymatic treatment was 37-49 mM.

| Enzyme | Conditions pH | T° C. | Buffer | Enzyme Concentrations | Free Amino groups mM | Enzyme Supplier | Product Code |
|---|---|---|---|---|---|---|---|
| Alcalase ® | 8 | 55 | MOPS | 8-769 mU/ml | 65-120 | CLEA Technologies | FE201 |
| *Aspergillus oryzae* acidic protease | 3.5 | 50 | glycine | 6-577 mU/ml | 11-124 | CLEA Technologies | FE207 |
| *Aspergillusoryzae* alkaline protease | 9 | 37 | Tris | 5-481 mU/ml | 32-169 | CLEA Technologies | FE208 |
| *Bacillus clausil* protease | 9 | 55 | Tris | 115-11500 mU/ml | 94-157 | CLEA Technologies | FE202 |
| *Bacillus lentus* protease | 9 | 55 | Tris | 96-9620 mU/ml | 48-132 | CLEA Technologies | FE203 |

TABLE 5-continued

Hydrolyzation of MBM medium using 14 different enzymes: hydrolyzation condition, range of tested enzyme concentrations, and the increase of free amino groups (mM) in the MBM medium after enzymatic treatment. The concentration of free amino groups in the MBM medium before the enzymatic treatment was 37-49 mM.

| Enzyme | Conditions pH | T° C. | Buffer | Enzyme Concentrations | Free Amino groups mM | Enzyme Supplier | Product Code |
|---|---|---|---|---|---|---|---|
| Bacillus stearothermophilis protease | 8 | 70 | MOPS | 3-288 mU/ml | 30-77 | CLEA Technologies | FE206 |
| Bacillus subtilis protease | 7 | 55 | MOPS | 7-763 mU/ml | 65-138 | CLEA Technologies | FE205 |
| Bromelain from pineapple stem | 5 | 60 | acetate | 77-7690 mU/ml | 30-88 | Sigma-Aldrich | B4882-10G |
| Collagenase type 2 | 7.5 | 50 | MOPS | 8-769 mU/ml | 17-50 | Worthington | LS004174 |
| Flavourzyme ®, protease mix from Aspergillus oryzae | 6.5 | 50 | MOPS | 385-38500 mU/ml | 169-588 | Sigma-Aldrich | P6110 |
| Papain | 6.5 | 65 | MOPS | 385-38500 mU/ml | 15-108 | CLEA Technologies | FE204 |
| Pepsin + 60° C. | 2 | 60 | — | 15-1540 µg/ml | 10-34 | AppliChem | A4289.2005 |
| Proteinase K | 8 | 50 | MOPS | 2-192 µg/ml | 34-74 | AppliChem | A3830.0025 |
| Trypsin from porcine pancreas | 8 | 37 | MOPS | 8-769 µg/ml | 15-37 | Sigma-Aldrich | T4799 |

Figure 5:
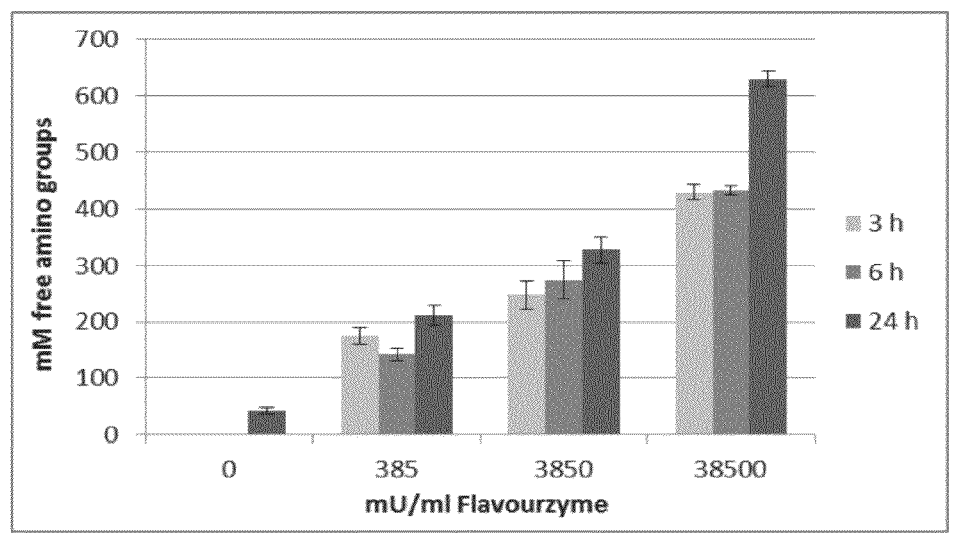
FIG. 5. Illustrates the effect of the hydrolyzation of MBM medium (180 g MBM per 1 liter) using different incubation times and Flavourzyme® concentrations on the end result of free amino groups in mM/liter. Error bars indicate standard deviations among three technical replicates.

The concentrations of the different tested hydrolyzation enzymes varied, depending on the original concentrations of the enzyme solutions, solubility of the enzymes, and recommendations of the manufacturers. However, the highest degree of hydrolyzation was obtained with the *Aspergillus oryzae* protease mix called Flavourzyme®. Flavourzyme® is commercially available from Novozymes Corporation, and it contains both endo- and exopeptidase activities. To study the capacity of Flavourzyme® further, MBM medium was hydrolyzed using different incubation times and different concentrations of Flavourzyme®. The results are shown by the figures, which shows that incubation times of less than 24 h were effective in the hydrolyzation of MBM using Flavourzyme® as measured by free amino groups in mM (millimole per liter) (FIG. 5). Amount of free amino groups as function of Flavourzyme® was seen to increase.

Combinations of different sequential enzyme treatments in the hydrolyzation of MBM were also tested. However, according to the preliminary results, hydrolyzation of MBM medium using the Flavourzyme® protease alone was the most promising option for processing MBM to produce free amino groups. The hydrolyzation conditions for Flavourzyme®, neutral pH (6.5) and mild heating (+50° C.), also are favorable.

Hydrolyzation with Flavourzyme® was followed by ammonification in anaerobic cultivation with AnaeroGen, Oxoid) using isolated strains ("Strain 385" and "Strain 393"), both belonging to the *Clostridium* genus, was tested. The tests demonstrated significantly higher (8-20 times better production) ammonia production in comparison to bacteria in experiment 1 (without hydrolyzation nor added glucose).

The following amount of Flavourzyme® was found to increase the ammonia production. Using 180 g MBM/liter and 385 mU Flavourzyme®/ml resulted to 700±140 mg/liter of ammonia production when fermented with Strain 385. Using 180 g MBM/liter and 38500 mU Flavourzyme®/ml resulted in 1150±130 mg/liter ammonia production when fermented with Strain 385.

Using 180 g MBM/liter and 385 mU Flavourzyme®/ml resulted in 800±150 mg/liter of ammonia production when fermented with Strain 393. Using 180 g MBM/liter and 38500 mU Flavourzyme®/ml resulted to 1140±98 mg/liter ammonia production when fermented with Strain 393.

A control experiment was conducted with MBM media, which had been incubated for 24 hours at +37 degrees Celsius without bacteria. The control experiments resulted in 63±23 mg/liter and 190±21 mg/liter for 385 mU/ml and 384000 mU/liters of ®® respectively.

Additionally, free amino groups were measured in the MBM media with 385 mU/ml Flavourzyme® and with 38 500 mU/ml of Flavourzyme®. Corresponding free amino groups were 130±7 mM (milliMole per liter) and 440±45 mM respectively after 18 hours of hydrolysation.

Example 6

Positive Effect on Ammonifizaton Using Selected Isolates

The ammonium production of selected *Clostridium* strains (385 and 393) was tested in different protein-rich media (MBM medium, fish meal medium, and rape cake medium,). The effect of Flavourzyme®-hydrolyzation on ammonium production was also shown.

MBM medium was prepared as described in earlier examples (180 g MBM, 2 g glucose, 1 l water). Fish meal medium was prepared from 180 g of fish meal (made of fish by-products of fish industry, protein content 630 g/kg), and 1 l water. Rape cake medium was prepared from 180 g of rape cake (consisting rape seeds from which oil has been removed, protein content 330 g/kg) and 1 l water. MBM, fish meal, and rape cake media were autoclaved in 10 ml aliquots.

All of the media were hydrolyzed as follows: the media were buffered with 50 mM MOPS (4-morpholinepropane-sulfonic acid), pH was adjusted at 6.5, and Flavourzyme® was added to concentration of 385 mU/1 ml of medium. The media were incubated at +50° C. for 18 hours, and the hydrolyzation reaction was stopped by heating the samples for 5 min at 100° C. Then, the pH of the media was adjusted at pH 8-8.5. The non-hydrolyzed control media were prepared as follows: the media were buffered with 50 mM MOPS and the pH was adjusted at pH 8-8.5. The success of the enzymatic hydrolyzation was ensured by measuring the concentration of free amino groups in all the media using the TNBS method described in earlier experiments.

The *Clostridium* strains ("Strain 385" and "Strain 393") were first cultivated using AnaeroGen, Oxoid) in BHI medium in an anaerobic jar at +37° C. for 16-24 h. From these, 70 µl of the culture was inoculated into hydrolyzed or non-hydrolyzed media. Ammonia production was measured after 24 h of anaerobic cultivation at +37° C. using an enzymatic determination kit for ammonia (Ammonia Assay Kit AA0100; Sigma-Aldrich).
Results:

Both of the *Clostridium* strains produced ammonium in all of the media. Hydrolyzation of the media using Flavourzyme® increased the ammonium production in all the media. Table 6 shows results of the experiment. It is clear from the results that selected strain of bacteria is able to produce ammonium on animal based materials and in addition to plant based material.

Ammonium production of *Clostridium* strains "Strain 385" and "Strain 393" in Flavourzyme®-hydrolyzed and non-hydrolyzed MBM medium, rape cake medium, and fish meal medium. The results are averages of three replicate experiments, each including three replicate measurements, and standard deviations of these 9 measurements are shown by Table 6, below.

TABLE 6

Ammonium production of *Clostridium* strains "Strain 385" and "Strain 393" in Flavourzyme ®-hydrolyzed and non-hydrolyzed MBM medium, rape cake medium, and fish meal medium. The results are averages of three replicate experiments, each including three replicate measurements, and standard deviations of these 9 measurements are shown.

| | Ammonia production (mg/l) | | |
|---|---|---|---|
| | Strain 385 | Strain 393 | No bacteria |
| MBM - non-hydrolyzed | 540 ± 92 | 270 ± 31 | 50 ± 5 |
| MBM - hydrolyzed with 385 mU/ml Flavourzyme ® | 700 ± 140 | 800 ± 150 | 63 ± 23 |
| Rape cake - non-hydrolyzed | 130 ± 22 | 150 ± 22 | 43 ± 11 |
| Rape cake - hydrolyzed with 385 mU/ml Flavourzyme ® | 350 ± 27 | 510 ± 100 | 130 ± 23 |
| Fish meal - non-hydrolyzed | 410 ± 100 | 430 ± 150 | 44 ± 14 |
| Fish meal - hydrolyzed with 385 mU/ml Flavourzyme ® | 610 ± 88 | 720 ± 130 | 120 ± 27 |

In addition, the free amino groups were measured in the media before and after hydrolyzation. The results confirmed that the enzymatic hydrolyzation was successful in all the media (Table 7.)

TABLE 7

Effect of 18 hours enzymatic hydrolyzation on the concentration of free amino groups in different media.

| | Free amino groups (mM) | |
|---|---|---|
| | No hydrolyzation | 385 mU/ml Flavourzyme |
| MBM | 30 ± 6 | 130 ± 7 |
| Rap cake | 21 ± 6 | 97 ± 4 |
| Fish meal | 56 ± 4 | 130 ± 6 |

In conclusion, the preferred embodiment for ammonification of organic material consists of steps of hydrolyzation of the material with Flavourzyme® followed by ammonification in presence of bacteria belonging to genus *Clostridium, beijerinckii* or *butyricum* or *perfringens* species (and particularly "Strain 385" or "Strain 393") and glucose or other carbohydrates in some cases.

INCORPORATION BY REFERENCE

Numerous references are cited throughout this application, each of which is incorporated by reference herein in its entirety. The present application also claims benefit from U.S. Provisional patent application Ser. No. 61/659,467, filed on Jun. 14, 2012, the disclosure of which is incorporated by reference herein in its entirety.

REFERENCES

Attwood et al. 1998 "Ammonia-Hyperproducing Bacteria from New Zealand Ruminants", APPLIED AND ENVIRONMENTAL MICROBIOLOGY, May 1998, p. 1796-1804.

Bladen, H. A., M. P. Bryant, and R. N. Doetsch. 1961. A study of bacterial species from the rumen which produce ammonia from protein hydrolysate. *Appl. Microbiol.* 9: 175-180.

Chourey, K.; Jansson, J.; VerBerkmoes, N.; Shah, M.; Chavarria, K. L.; Tom, L. M.; Brodie, E. L.; Hettich, R. L. 2010. Direct cellular lysis/protein extraction protocol for soil metaproteomics. *Journal of Proteome Research* 9: 6615-6622.

Chen, G., and J. B. Russell. 1988. Fermentation of peptides and amino acids by a monensin-sensitive ruminal *Peptostreptococcus. Appl. Environ. Microbiol.* 54:2742-2749.

Eschenlauer, S. C. P., N. McKain, N. D. Walker, N. R, McEwan, C. J. Newbold, and R. J. Wallace. 2002. Ammonia production by rumen microorganisms and enumeration, isolation, and characterization of bacteria capable of growth on peptides and amino acids from the sheep rumen. *Appl. Environ. Microbiol.* 68:4925-4931.

Guštin 5., Marinšek-Logar R. 2011. Effect of pH, temperature and air flow rate on the continuous ammonia stripping of the anaerobic digestion effluent. *Process Safety and Environmental Protection* 89: 61-66

Hungate R. E. 1969. A Roll Tube Method For Cultivation of Strict Anaerobes" in *Methods of Microbiology*, Vol. 111pps. 117-132, Academic Press, London.

Miller G L. 1959. Use of dinitrosalicylic acid reagent for determination of reducing sugar. *Anal. Biochem.* 31: 426-428.

Navarrete del Toro M A, Garda-Carrẽno F L. 2002. Evaluation of the Progress of Protein Hydrolysis. *Current Protocols in Food Analytical Chemistry* B2.2.1-B2.2.14.

Nelson, N. O., Mikkelsen, R. L. & Hesterberg, D. L. 2003. Struvite precipitation in anaerobic swine lagoon liquid: effect of pH and Mg:P ratio and determination of rate constant. *Bioresource Technoology* 89: 229-236.

Paster, B. J., J. B, Russell, C. M. J. Yang, J. M. Chow, C. R. Woese, and R. Tanner. 1993. Phylogeny of the ammonia-producing ruminal bacteria *Peptostreptococcus anaerobius, Clostridium sticklandii* and *Clostridium aminophilum* sp. nov. *Int. J. Syst. Bacteriol.* 43: 107-110.

Russell, J. B., H. J. Strobel, and G. Chen. 1988. Enrichment and isolation of a ruminal bacterium with a very high specific activity of ammonia production. *Appl. Environ. Microbiol.* 54:872-877.

Rychlik, J. L., and J. B. Russell. 2000. Mathematical estimations of hyper-ammonia producing ruminal bacteria and evidence for bacterial antagonism that decreases ruminal ammonia production. *FEMS Microbiol. Ecol.* 32: 121-128.

Schulze-Rettmer, R., von Fircks, R. & Simbach, B. 2001. MAP precipitation—pilot plant investigation in Germany. *Environmental Technology.*

Smil, V. 2001. Evolution of Ammonia Synthesis. In: Enriching the Earth. Fritz Haber, Carl Bosch, and the Transformation of World Food Production. p, 109-132. MIT Press. Cambridge (USA), London. ISBN 0-262-19449-X.

Gowariker, V., Krishnamurthy V. N., Gowariker S., Dhanorkar, M., Kalyani P. 2009. Ammonification. In: The Fertilizer Encyclopedia. p. 41-42. John Wiley & Sons, Inc., Hoboken, N.J.

US Geological Survey. 2012. Nitrogen (fixed)-ammonia. US Department of Interior, Mineral Commodity Summaries, p. 112-113. US Department of Interior, US Geological Survey.

Vince A J, Burridge S M. 1980. Ammonia production by intestinal bacteria: the effects of lactose, lactulose and glucose. *J Med Microbiol* 13: 177-91.

Whitehead T R, Cotta M A. 2004. Isolation and identification of hyper-ammonia producing bacteria from swine manure storage pits. *Curr Microbiol* 48: 20-26.

What is claimed is:

1. A process for producing ammonia or ammonium from an organic material, the method comprising:
   (a) contacting the organic material with at least one hydrolytic enzyme, in an aqueous medium, to produce a hydrolyzed or partially hydrolyzed organic material suitable for microbial fermentation, in the aqueous medium;
   (b) fermenting the product of step (a) in the presence of at least one microorganism capable of ammonification, wherein the fermenting is under conditions, and for a sufficient period of time, to produce a fermentation product that comprises ammonia or ammonium;
   wherein the organic material comprises nitrogenous compounds suitable for conversion to ammonia or ammonium; and
   wherein the microorganism is a bacterial isolate selected from the group consisting of a bacterial isolate deposited as VTT-E-123272, a bacterial isolate deposited as VTT-E-123273, and combinations thereof.

2. The process of claim. 1, wherein step (b) is conducted with a medium enriched with a carbohydrate suitable for promoting microbial growth.

3. The process of claim 1, wherein the bacterial isolate is deposited as VTT-E-123272.

4. The process of claim 1, wherein the bacterial isolate is deposited as VTT-E-123273.

5. The process of claim 1, wherein the hydrolytic enzyme is selected from the group consisting of an amylase, cellulase, protease, phytase and combinations thereof.

6. The process of claim 1, wherein the hydrolytic enzyme is selected from the group consisting of Alcalase®, *Aspergillus oryzae* acidic protease, *Aspergillus oryzae* alkaline protease, *Bacillus clausil* protease, *Bacillus lentus* protease, *Bacillus stearothemophilis* protease, *Bacillus subtillus* protease, bromelain, collagenase type 2, Flavourzyme® protease mix from *Aspergillus oryzae*, papain, pepsin, proteinase K, porcine pancrease trypsin and combinations thereof.

7. The process of claim 1, wherein the hydrolytic enzyme is a Flavourzyme® present in the medium in a concentration of about 300 mU through about 40,000 mU.

8. The process of claim 1, further comprising recovering ammonia or ammonium from the fermentation product.

9. The process of claim 8, wherein the ammonia or ammonium is recovered mechanically or is precipitated.

10. The process of claim 8, wherein the ammonia or ammonium is recovered by the steps of:
    (a) dehydrating the fermentation product to provide a dry fermentation product;
    (b) collecting ammonia or ammonium-water or gas mixture released during the dehydrating step (a); and
    (c) recovering the ammonia or ammonium.

11. The process of claim 8 that further comprises:
    (d) converting the recovered ammonia or ammonium to a unified form; and
    (e) recovering the unified form;
    wherein the unified form is selected from the group consisting of: ammonium nitrate, ammonium sulphate, ammonium chloride, ammonium phosphate, diammonium phosphate and monoammonium phosphate and combinations thereof.

12. The process of claim 1, wherein the nitrogenous compounds are amines or proteins.

13. The process of claim 1 wherein the organic material is selected from the group consisting of meat-and bone meal (MBM), slaughterhouse waste, whey, municipal waste, fish meal, food industry waste streams and combinations thereof.

14. The process of claim 1 wherein the food industry waste streams are selected from the group consisting of meals of meat-and-bone, fish, and feathers, beet root, legumes, fruit, and sugar industry waste.

15. The process of claim 1 wherein the fermenting step is conducted at a pH ranging from about pH 2 through about 14 and at a temperature ranging from about 20° C. through about 70° C.

16. The process of claim 15 wherein fermenting step is conducted at a pH ranging from about pH 6.0 to about pH 9.0, and at a temperature ranging from about 30° C. to about 45° C.

17. The process of claim 1 wherein the MBM is present in the hydrolysis step in a concentration ranging from about 50 g/l to about 250 g/l.

18. The process of claim 1 wherein the hydrolysis step is conducted at a pH ranging from about pH 2 through about pH 14, and at a temperature ranging from about 20° C. through about 80° C.

19. The process of claim 1 wherein the hydrolysis step is conducted at a pH ranging from about 5 through about pH 9, and at a temperature ranging from about 45° C. through about 60° C.

20. An isolated *Clostridium* bacterial strain deposited as VTT-E-123272.

21. An isolated *Clostridium* bacterial strain deposited as VTT-E-123273.

22. The process of claim 1, wherein the MBM is obtained by a process comprising pressure sterilizing, drying and defatting waste products of animal processing.

23. The process of claim 22 wherein the waste products of animal processing are selected from the group consisting of feathers, hair, wool, horn, hooves, skin, meat, bone and combinations thereof.

* * * * *